United States Patent
Ogawa

(10) Patent No.: US 9,737,432 B2
(45) Date of Patent: Aug. 22, 2017

(54) NAIL CORRECTING DEVICE

(71) Applicant: ACTMENT CO., LTD, Kasukabe-shi, Saitama (JP)

(72) Inventor: Akira Ogawa, Kasukabe (JP)

(73) Assignee: ACTMENT CO., LTD, Kasukabe (JP)

( * ) Notice: Subject to any disclaimer, the term of this patent is extended or adjusted under 35 U.S.C. 154(b) by 0 days.

(21) Appl. No.: 14/976,836

(22) Filed: Dec. 21, 2015

(65) Prior Publication Data

US 2017/0007437 A1   Jan. 12, 2017

(30) Foreign Application Priority Data

Jul. 10, 2015 (JP) .................................. 2015-139243

(51) Int. Cl.
  *A61B 17/00* (2006.01)
  *A61F 5/11* (2006.01)

(52) U.S. Cl.
  CPC ..................... *A61F 5/11* (2013.01)

(58) Field of Classification Search
  CPC ........ A61F 5/11; A61F 5/019; A61F 5/05875; A61F 5/10
  USPC .............. 606/201; 602/30, 31; 128/893, 894
  See application file for complete search history.

(56) References Cited

U.S. PATENT DOCUMENTS

| | | | |
|---|---|---|---|
| 2,405,547 A * | 8/1946 | Armagost ................. | A61F 5/11 602/31 |
| 2,613,667 A | 10/1952 | Stanley | |
| 3,173,416 A | 3/1965 | Rederich | |
| 5,318,508 A | 6/1994 | Osthold et al. | |
| 2009/0078277 A1 * | 3/2009 | Uemura ..................... | A61F 5/11 132/73.5 |
| 2011/0282257 A1 * | 11/2011 | Suzuki ....................... | A61F 5/11 602/31 |

FOREIGN PATENT DOCUMENTS

| | | |
|---|---|---|
| JP | 2007-244851 A | 9/2007 |
| JP | 2012-095800 A | 5/2012 |
| JP | 5009434 B1 | 8/2012 |
| JP | 2012-176228 A | 9/2012 |
| JP | 2015-089503 A | 5/2015 |

OTHER PUBLICATIONS

Linear. (n.d). Dictionary.com Unabridged. Retrieved Jan. 10, 2017 from Dictionary.com website http://www.dictionary.com/browse/linear.*
Nov. 15, 2016 Search Report issued in European Patent Application No. 15201448.6.

* cited by examiner

*Primary Examiner* — Wade Miles
*Assistant Examiner* — Kankindi Rwego
(74) *Attorney, Agent, or Firm* — Oliff PLC

(57) ABSTRACT

A nail correcting device made of an elastic material includes: a pair of holding pieces arranged side by side in a predetermined direction; and a connecting piece connecting the holding pieces to each other, the pair of holding pieces each including: a body at least partly in an arc within a plane intersecting with the predetermined direction; and a pair of first and second distal edges connected to both ends of the body to hold a nail. The pair of first and second distal edges are spaced from each other along the predetermined direction at an inner side and an outer side.

5 Claims, 19 Drawing Sheets

NAIL CORRECTING DEVICE

The entire disclosure of Japanese Patent Application No. 2015-139243 filed Jul. 10, 2015 is expressly incorporated by reference herein.

FIELD OP THE INVENTION

The present invention relates to a nail correcting device for correcting deformed nails such as an ingrown nail and a pincer nail.

BACKGROUND ART

An ingrown nail causes inflammation because the side edges of the ingrown nail are curved inward to press or dig into a soft tissue (e.g., a toe skin) with pain, which may result in symptoms such as granulation and pyogenesis. It should be noted that many patients with ingrown nails also have pincer nails, the side edges of which curl inward.

There have been proposed typical nail correcting devices for correcting deformed nails such as a pincer nail and an ingrown nail.

A typical example of the nail correcting devices includes a cylindrical body provided with a slit extending from a first end to a second end of the cylindrical body (see Patent Literature 1: Japanese Patent No. 5009434).

The cylindrical body of the nail correcting device of Patent Literature 1 includes: plural pairs of holding teeth divided in a longitudinal direction of the cylindrical body by a plurality of dividing grooves circumferentially extending around the cylindrical body from the slit; and connecting pieces that connect the holding teeth.

The holding teeth of each pair face each other across the slit to hold the distal edge of a nail. The nail correcting device is attached by widening the slit and inserting the distal end of a nail to be corrected in the slit.

The plurality of holding teeth of the nail correcting device of Patent Literature 1 are arranged in the longitudinal direction of the cylindrical body from the first end to the second end, and each hold the distal edge of the nail.

However, although nail shape and nail thickness vary from person to person, a distance between distal edges of the holding teeth for holding a nail is set at a predetermined value.

It is thus difficult to attach the nail correcting device to the nails of some people. For instance, whereas the average nail thickness of humans is approximately 0.7 mm, the distance between the distal edges of the holding teeth is in a range from 1.0 to 1.2 mm. Although the distance between the distal edges of the holding teeth is slightly larger than the average nail thickness, the plurality of holding teeth can reliably hold a nail due to the curvature of the nail when the nail correcting device is attached to the nail. The nail correcting device is thus unlikely to be detached.

However, some men have thick nails with a thickness of approximately 2.0 mm. When the distance between the distal edges is in a range from 1.0 to 1.2 mm, the nail correcting device is difficult to attach to such thick nails.

When the distance between the distal edges of the holding teeth is increased so that people with thick nails can use the nail correcting device, the nail correcting device is unsuitable for people having nails with a normal thickness approximately in a range from 0.7 to 1.0 mm, and thus is to be detached from the nail.

In consideration of the fact that nail thickness varies from person to person, plural kinds of nail correcting devices with different distances between the distal edges of the holding teeth may be prepared. However, this results in an increase in the variety of the nail correcting devices and thus in an increase in production costs. Further, it is difficult for a user to choose a suitable nail correcting device.

SUMMARY OF THE INVENTION

An object of the invention is to provide a nail correcting device widely usable for patients with deformed nails different in nail thickness and shape.

According to an aspect of the invention, a nail correcting device made of an elastic material includes: a pair of holding pieces arranged side by side in a predetermined direction; and a connecting piece connecting the holding pieces to each other, the pair of holding pieces each including: a body at least partly in an arc within a plane intersecting with the predetermined direction; and a pair of first and second distal edges connected to both ends of the body to hold a nail, the pair of first and second distal edges being spaced from each other along the predetermined direction at an inner side and an outer side.

The elastic material is not particularly limited. Examples of the elastic material include superelastic materials such as nickel titanium, elastic bodies having shape-memory properties, elastic materials such as stainless steel, titanium alloy, copper alloy and irons, and elastic materials such as plastics.

One of the pair of distal edges of the nail correcting device is put on a distal back surface of a nail, and then the nail correcting device is bent to put the other distal edge on a distal front surface of the nail. The distal front and back surfaces of the nail are thus held by the pair of distal edges (i.e., the first and second distal edges), which are vertically distanced from each other, to correct the nail.

In the above aspect, the first and second distal edges of each of the pair of holding pieces are spaced from each other in the predetermined direction at the inner side and the outer side. A large space is thus created between the first and second distal edges as compared with a typical device including a pair of holding teeth facing each other. Since the nail correcting device has the large space for the nail to be inserted when the nail correcting device is attached to the nail, the nail correcting device is available for a wide variety of nails with different thicknesses, and the holding pieces can be easily set on the nail.

Further, a distance between the first and second distal edges of each of the pair of holding pieces is comparable to that of a typical device. The nail can thus be held with the elastic force of the body and the first and second distal edges of each of the pair of holding pieces, thereby restraining the nail correcting device from being detached from the nail. Further, the holding pieces are each in an arc when seen within the plane intersecting with the predetermined direction. The concentration of stress on a specific portion is thus prevented as compared with an instance in which the holding pieces each have a bent portion, which results in prevention of, for instance, breakage of the holding pieces.

In the above aspect, it is preferable that the connecting piece extends in the predetermined direction, and has ends each connected to the first distal edge at the inner side of each of the pair of holding pieces.

When the pair of holding pieces are situated at both sides of the elongated connecting piece, the structure of the nail correcting device can be simplified.

In the above aspect, it is preferable that the body includes an arc portion in an arc within a plane orthogonal to the predetermined direction, the arc portion being connected to the second distal edge at the outer side of each of the pair of holding pieces.

The first distal edge and the second distal edge, which is connected to the arc portion, can hold the nail at close positions in the distal front and back surfaces of the nail with an intense holding force. This results in an increase in the corrective force. Further, the first distal edge can serve as a mark for holding the distal edge of the nail between the first and second distal edges, so that the nail correcting device can be easily attached.

In the above aspect, it is preferable that the body includes a helical portion having an end connected to the first distal edge at the inner side of each of the pair of holding pieces.

Since the helical portion increases an elastically deformable range to make the first and second distal edges easily separable from each other. The nail correcting device can thus be easily attached.

In the above aspect, it is preferable that the body includes a linear portion provided along a longitudinal direction of the connecting piece, the linear portion having an end connected to the first distal edge at the inner side of each of the pair of holding pieces.

When the connecting piece and the linear portion are in alignment with each other, the structure of the nail correcting device can be simplified.

In the above aspect, it is preferable that the connecting piece includes a V-shaped portion having distal ends and a base end, the distal ends being each connected to the first distal edge at the inner side of each of the pair of the holding pieces, the base end holding the nail in combination with the first distal edge of each of the pair of the holding pieces.

When the connecting piece includes the helical V-shaped portion, and the base end and the distal ends thereof hold the nail, the nail can be reliably held. This results in an increase in the corrective force.

DESCRIPTION OF EMBODIMENT(S)

Figure 1:
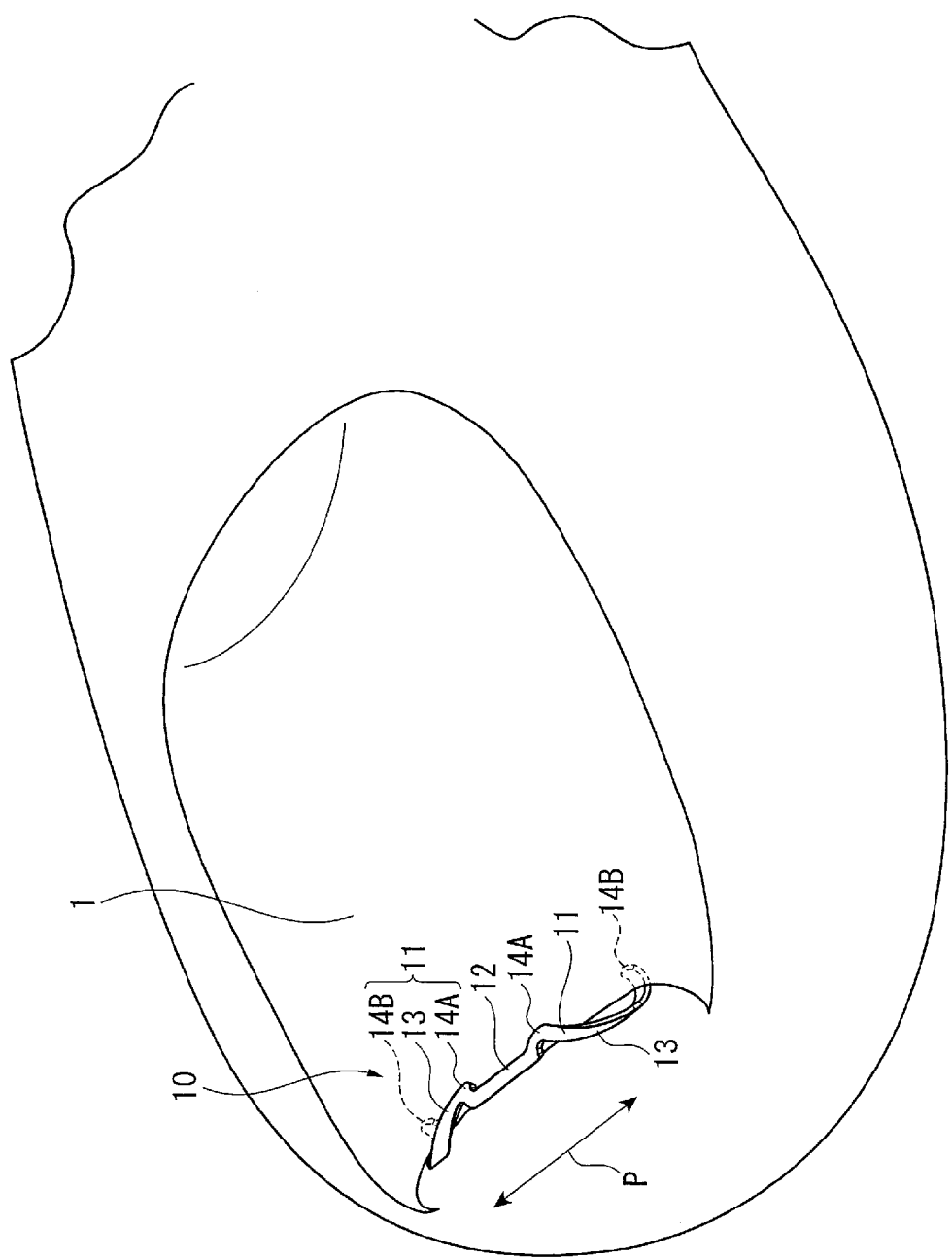
FIG. 1 is a perspective view showing a nail correcting device according to a first exemplary embodiment of the invention attached to a nail.
Figure 2:
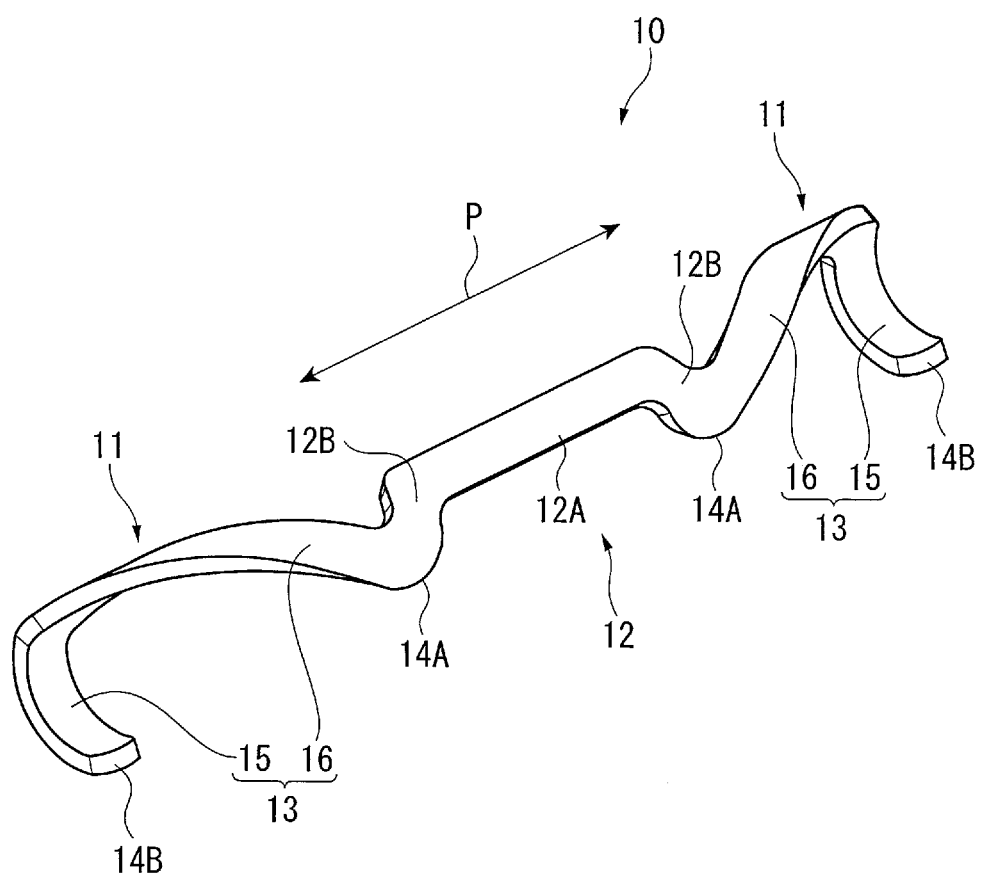
FIG. 2 is a perspective view showing the nail correcting device according to the first exemplary embodiment.

Exemplary embodiment(s) of the invention will be described below with reference to the attached drawings. In the description of the embodiment(s), the same components are attached with the same reference signs, and the explanation thereof is omitted.

First Exemplary Embodiment

A first exemplary embodiment of the invention will be described with reference to FIGS. 1 to 5.

As shown in FIGS. 1 to 4, a nail correcting device 10 of the first exemplary embodiment, which is designed to be attached to a nail 1 (e.g., a pincer nail or an ingrown nail) to correct the nail 1, includes a pair of holding pieces 11 arranged side by side in one direction P, and a connecting piece 12 connecting the holding pieces 11. The whole of the nail correcting device 10 is made of a superelastic material.

The pair of holding pieces 11 each include a body 13 in an arc in a projection view on a plane orthogonal to the direction P, and arc-shaped distal edges 14A, 14B connected to both ends of the body 13.

A distal edge of the nail 1 to be corrected is inserted and held between the distal edges 14A, 14B. The distal edge 14A is brought into contact with a distal front surface of the nail 1, and the distal edge 14B is brought into contact with a distal back surface of the nail 1.

In the first exemplary embodiment, the pair of distal edges 14A, 14B are spaced from each other along the direction P, the distal edge 14A being situated at an inner side, i.e., being near the connecting piece 12, the distal edge 14B being situated at an outer side, i.e., being opposite to the distal edge 14A across the body 13.

The body 13 includes: an arc portion 15 in an arc within the plane orthogonal to the direction P, the arc portion 15 having a first end connected to the distal edge 14B situated at the outer side; and a helical portion 16 having a first end connected to a second end of the arc portion 15 and a second end connected to the distal edge 14A situated at the inner side.

A center axis of the arc portion 15, a center axis of the helical portion 16, and center axes of the distal edges 14A, 14B coincide with one another. These center axes are parallel with the direction P.

The connecting piece 12 includes an elongated portion 12A elongated in the direction P, and projections 12B connected to both ends of the elongated portion 12A. A distal end of each of the projections 12B is connected to the distal edge 14A situated at the inner side.

An adhesive (not shown) is provided between the elongated portion 12A and the nail 1. The adhesive may be provided not only between the elongated portion 12A and the nail 1, but also in a U-shaped space in a plan view defined by the elongated portion 12A, each of the projections 12B and the distal edge 14A.

The adhesive ("bonder") may contain ethyl cyanoacrylate or methyl polymethacrylate. Further, a topcoat (an aqueous acrylic), a gel nail polish (a gel resin curable by ultraviolet irradiation), and a curing agent (an activator) are usable. The curing agent may contain acetic ether or gammabuthyrolactone. Similarly to a urethane resin, the bonder and the activator, which are transparent and three-dimensionally curable, are fully cured in several minutes. It is further preferable that the adhesive is impregnated with a medical agent such as a therapeutic agent for fungal infection or an antibacterial agent.

A longitudinal dimension L of the nail correcting device 10 of the first exemplary embodiment, which is determined depending on the width of the nail 1 to be corrected, falls within a range, for instance, approximately from 5 mm to 20 mm. An outer diameter D of the body 13, which is determined depending on the curvature of the nail 1 to be corrected, falls within a range, for instance, approximately from 1.2 mm to 4.0 mm. A thickness T of the body 13, which is determined with reference to a relationship with a material used to make the nail correcting device 10, falls within a range, for instance, approximately from 0.02 mm to 0.5 mm.

Figure 3:
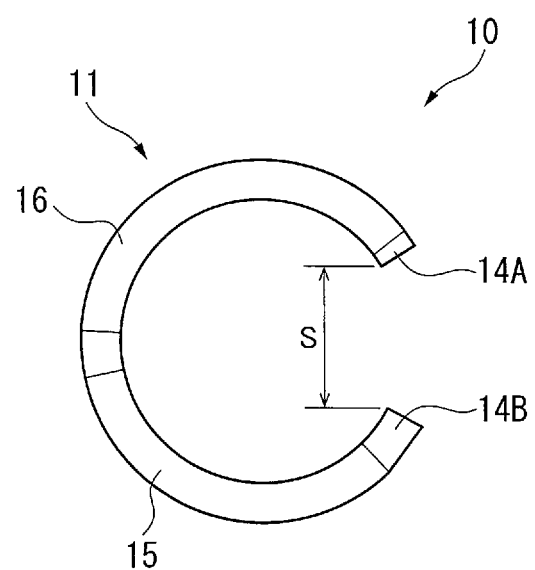
FIG. 3 is a side view showing the nail correcting device according to the first exemplary embodiment.
Figure 4:
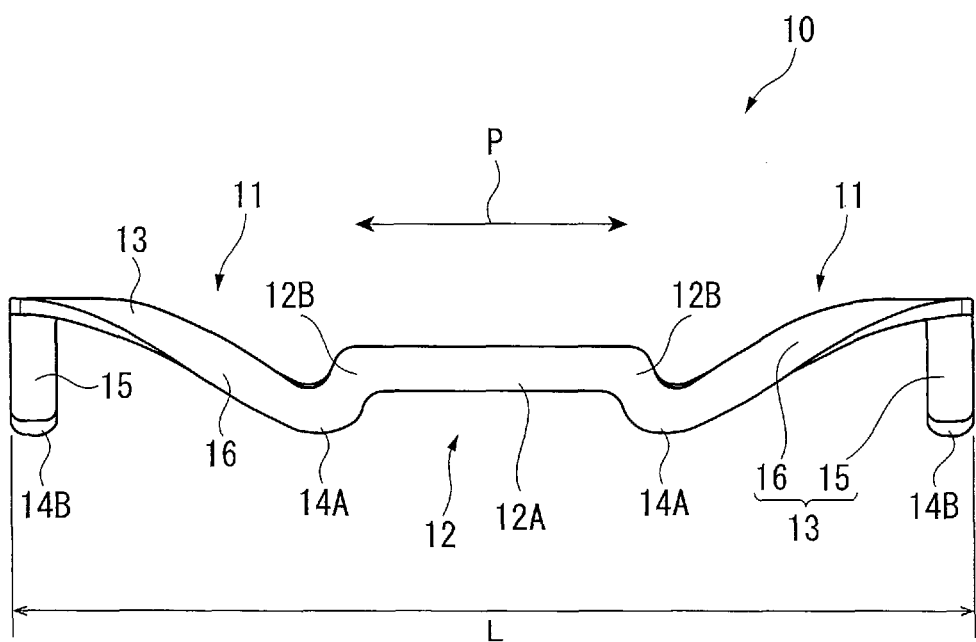
FIG. 4 is a front view showing the nail correcting device according to the first exemplary embodiment.

As shown in FIG. 3, a space S between a distal end of the distal edge 14A and a distal end of the distal edge 14B defined within the plane orthogonal to the direction P is determined depending on the thickness and curvature of the nail 1 to be corrected. For instance, the space S is in a range approximately from 0.3 mm to 2.5 mm, preferably in a range approximately from 0.5 mm to 2.0 mm, and more preferably in a range approximately from 0.8 mm to 1.5 mm.

Figure 5:
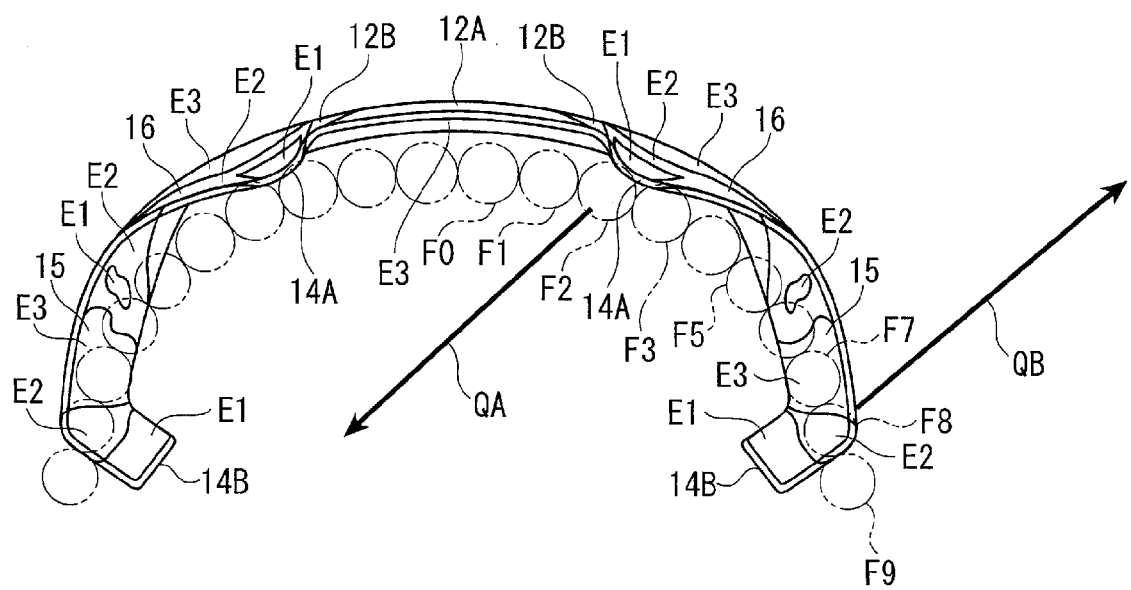
FIG. 5 schematically shows an analysis result by a finite element method according to the first exemplary embodiment.
Figure 6:
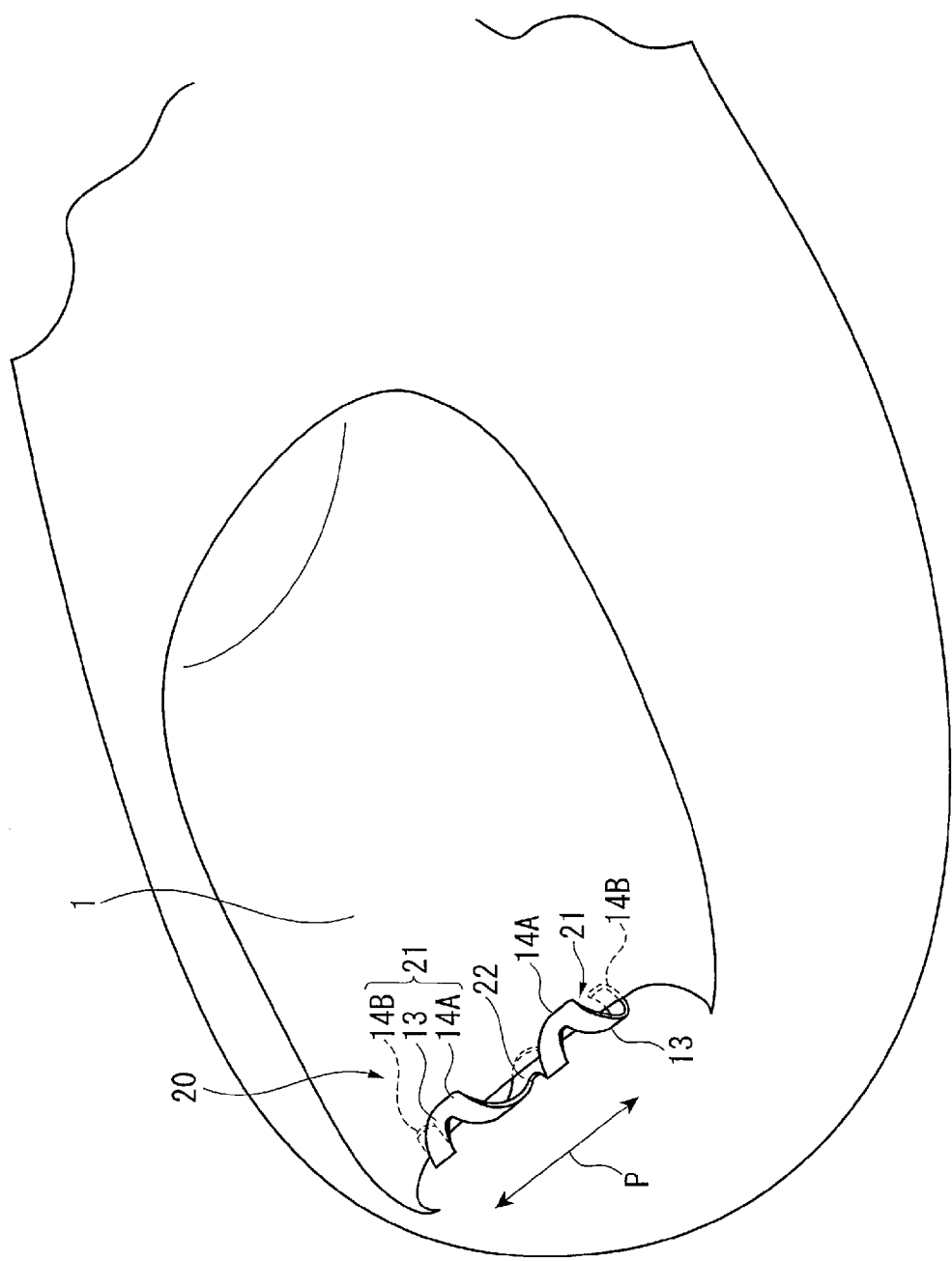
FIG. 6 is a perspective view showing a nail correcting device according to a second exemplary embodiment of the invention attached to a nail.
Figure 7:
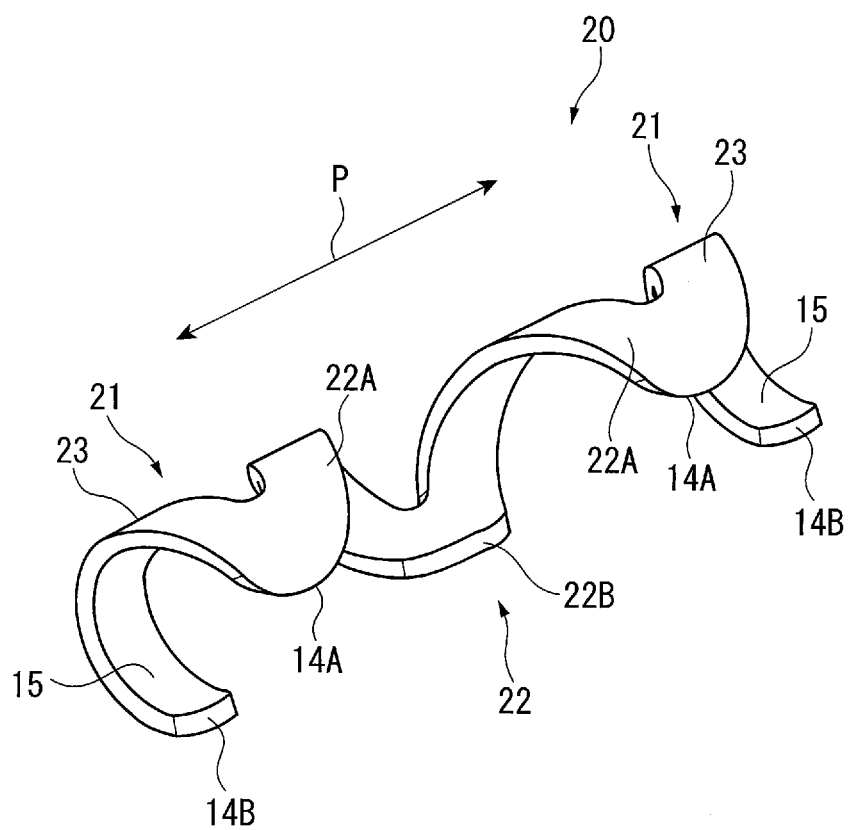
FIG. 7 is a perspective view showing the nail correcting device according to the second exemplary embodiment.
Figure 8:
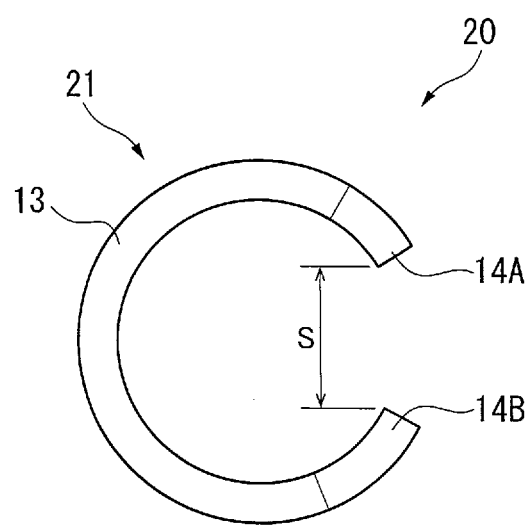
FIG. 8 is a side view showing the nail correcting device according to the second exemplary embodiment.
Figure 9:
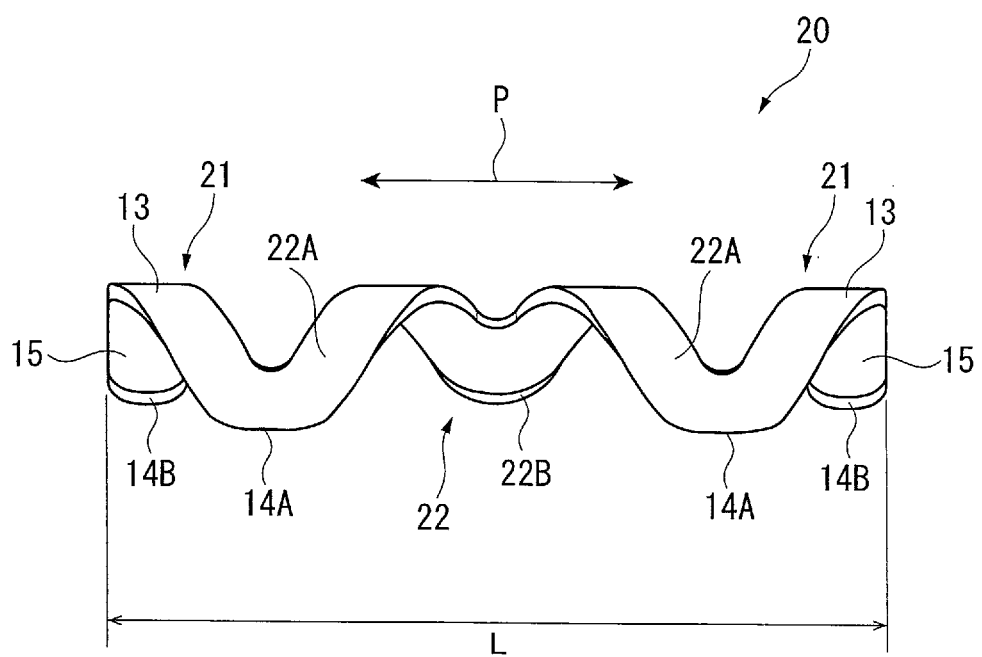
FIG. 9 is a front view showing the nail correcting device according to the second exemplary embodiment.

FIG. 5 schematically shows an analysis result of the nail correcting device 10 of the first exemplary embodiment by a finite element method.

In FIG. 5, reference signs F0, F1, F2 . . . F8 and F9 denote positions in the nail. Of the above positions in the nail, ones where stress acts on the nail correcting device 10 are denoted by reference signs E1, E2 and E3 in the descending order of the intensity of the stress. Reference signs QA, QB (arrows from the positions F2, F8) show nail corrective forces generated at the maximum curvature. The corrective forces QA, QB were each approximately 3 N.

As is evident from FIG. 5, it has been demonstrated that the corrective force QA (the maximum value) is generated at a position corresponding to the distal edge 14A, and the corrective force QB (the maximum value) is generated at a position corresponding to the distal edge 14B in the first exemplary embodiment. The corrective forces QA, QB acts in mutually opposite directions. It should be noted that merely the corrective forces acting on the half of the nail are described above with reference to FIG. 5, but the same applies to the other half. It should also be noted that the corrective forces are increased/reduced depending on the thickness and/or width of the plate.

For manufacturing the nail correcting device 10, a cylindrical material (i.e., a cylindrical pipe with a slit made of a superelastic material, a shape-memory alloy, or the like) for the nail correcting device is machined into a predetermined shape using, for instance, a laser machine (not shown).

Alternatively, etching may be performed. The cylindrical material (i.e., the cylindrical pipe with the slit made of a superelastic material, a shape-memory alloy, or the like) is prepared beforehand. The cylindrical material is degreased, rinsed, neutralized and rinsed. After such a surface treatment, a surface of the cylindrical material is coated with a resist (sensitizer), and then subjected to an exposure process, a development process, and the other.

Attachment of Nail Correcting Device

First, the distal edge 14B (the outer distal edge) of one of the pair of holding pieces 11 is put on the distal back surface of the nail 1, and then the nail correcting device 10 is bent to bring the two distal edges 14A (the inner distal edges) into contact with the distal front surface of the nail 1 toward the proximal nail fold from the distal edge of the nail 1. Subsequently, the other one of the holding pieces 11 is bent to put the other distal edge 14B (the other outer distal edge) on the distal back surface of the nail 1. The adhesive is applied between the nail correcting device 10 and the nail 1.

When the nail correcting device 10 is attached to the nail 1, the nail 1 is held with the elastic force of the body 13 and the distal edges 14A, 14B of each of the pair of holding pieces 11.

The first exemplary embodiment can thus provide the following effects (1) to (5).

(1) The pair of holding pieces 11 each include the distal edges 14A, 14B spaced along the direction P. A space between the distal ends of the pair of distal edges 14A, 14B is thus increased as compared with an instance in which they face each other within the plane orthogonal to the direction P, so that the nail correcting device 10 can be easily attached irrespective of the thickness of the nail 1. When the nail correcting device 10 is attached to the nail 1, the nail 1 is reliably held between the distal edges 14A, 14B, so that the nail correction device 10 is prevented from being detached from the nail 1.

(2) The holding pieces 11 are each in an arc when seen within the plane orthogonal to the direction P. The concentration of stress on a specific portion is thus prevented as compared with an instance in which the holding pieces 11 each have a bent portion, which results in prevention of troubles such as the breakage of the holding pieces 11.

(3) The connecting piece 12 includes the elongated portion 12A, both ends of which define the projections 12B each connected to the inner distal edge 14A. The structure of the nail correcting device 10 can thus be simplified. Further, the adhesive used to attach the nail correcting device 10 to the nail 1 accumulates in the U-shaped space in a plan view defined by the elongated portion 12A and each of the projections 12B at both ends of the elongated portion 12A, so that the nail correcting device 10 can be reliably bonded to the nail 1.

(4) The holding pieces 11 each include the body 13 with both ends connected to the distal edge 14A and the distal edge 14B, and the body 13 includes the arc portion 15 in an arc within the plane orthogonal to the direction P. The inner distal edge 14A and the outer distal edge 14B can thus hold the nail 1 at close positions on the distal edge of the nail 1 with an intense holding force, which results in an increase in the corrective force. Further, since the distal edge 14A can serve as a mark for holding the distal edge of the nail 1 between the distal edges 14A, 14B, the nail correcting device can be easily attached.

(5) The body 13 includes a helical portion 16 having the end connected to the distal edge 14A. The helical portion 16 increases an elastically deformable range of the body 13, so that the distal edge 14A and the distal edge 14B can be easily separated from each other. The nail correcting device 10 can thus be easily attached to the nail 1.

Second Exemplary Embodiment

Next, a second exemplary embodiment of the invention will be described with reference to FIGS. 6 to 10.

As shown in FIGS. 6 to 9, a nail correcting device 20 of the second exemplary embodiment includes a pair of holding pieces 21 arranged side by side in the direction P, and a connecting piece 22 connecting the holding pieces 21. The whole of the nail correcting device 20 is made of a superelastic material (e.g., nickel titanium).

The pair of holding pieces 21 each include the body 13, and the arc-shaped distal edges 14A, 14B connected to both ends of the body 13.

The connecting piece 22 is a V-shaped portion, and has distal ends 22A each connected to the distal edge 14A situated at the inner side.

The connecting piece 22 (V-shaped portion) is helical and has the same diameter as that of the body 13 including a helical portion. A base end 22B of the connecting piece 22 is brought into contact with the distal back surface of the nail 1 as well as the distal edge 14B. In other words, in the second exemplary embodiment, the two distal edges 14A, the two distal edges 14B, and the base end 22B hold the nail 1.

It should be noted that the distal edge 14B and the distal edge 14A of one of the holding pieces 21, the base end 22B, and the distal edge 14A and the distal edge 14B of the other holding piece 21 are spaced from one another in this sequence along the direction P at the same distance. It should be noted that the connecting piece 22 may be in any shape different from a V-shape, such as a U-shape. In other words, as long as the base end 22B is obliquely situated relative to the distal edges 14A at the right and left sides of the base end 22B to hold the nail, the shape of the connecting piece 22 is not particularly limited.

Figure 10:
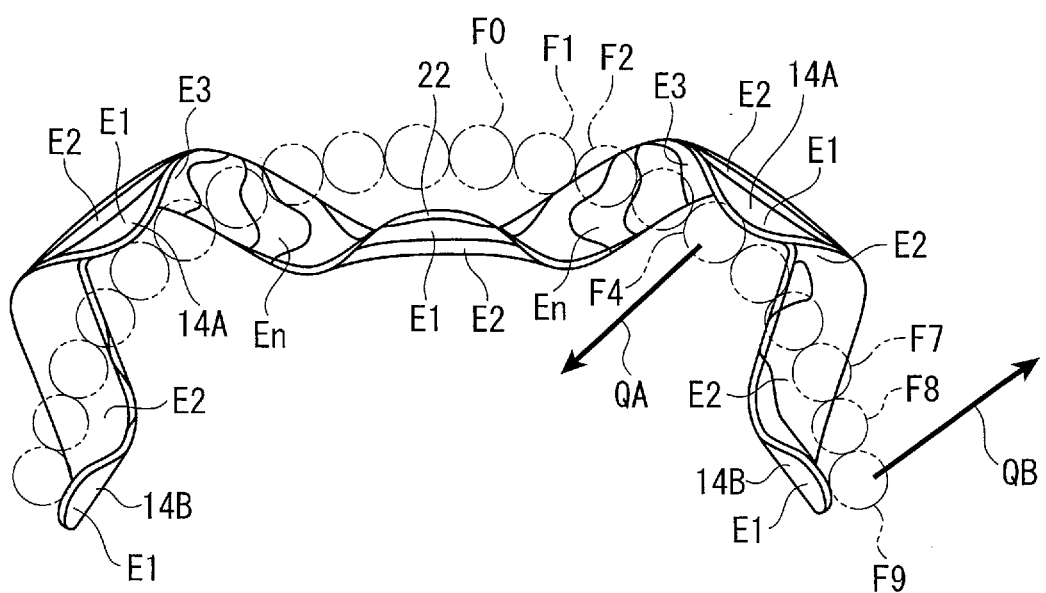
FIG. 10 schematically shows an analysis result by a finite element method according to the second exemplary embodiment.
Figure 11:
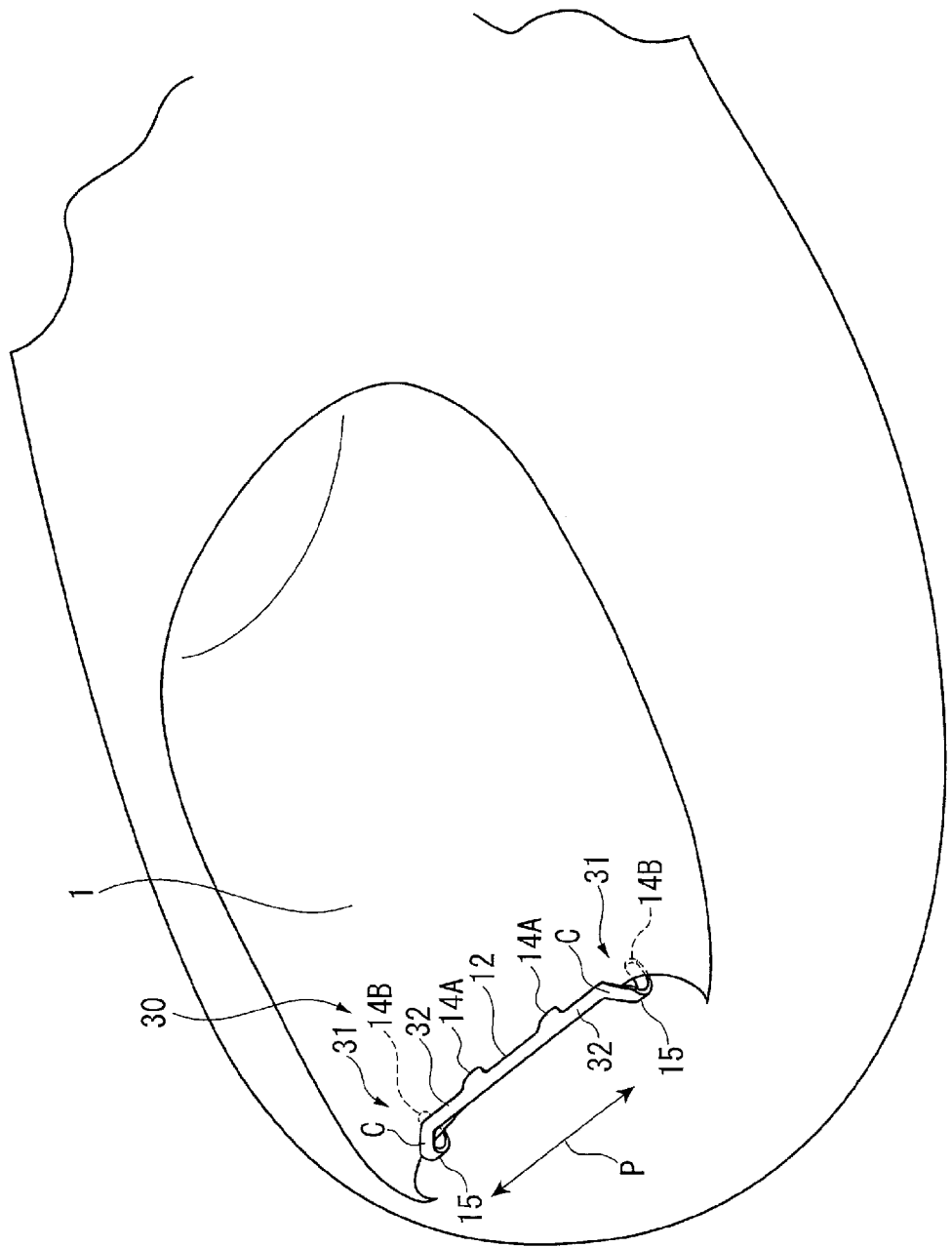
FIG. 11 is a perspective view showing a nail correcting device according to a third exemplary embodiment of the invention attached to a nail.
Figure 12:
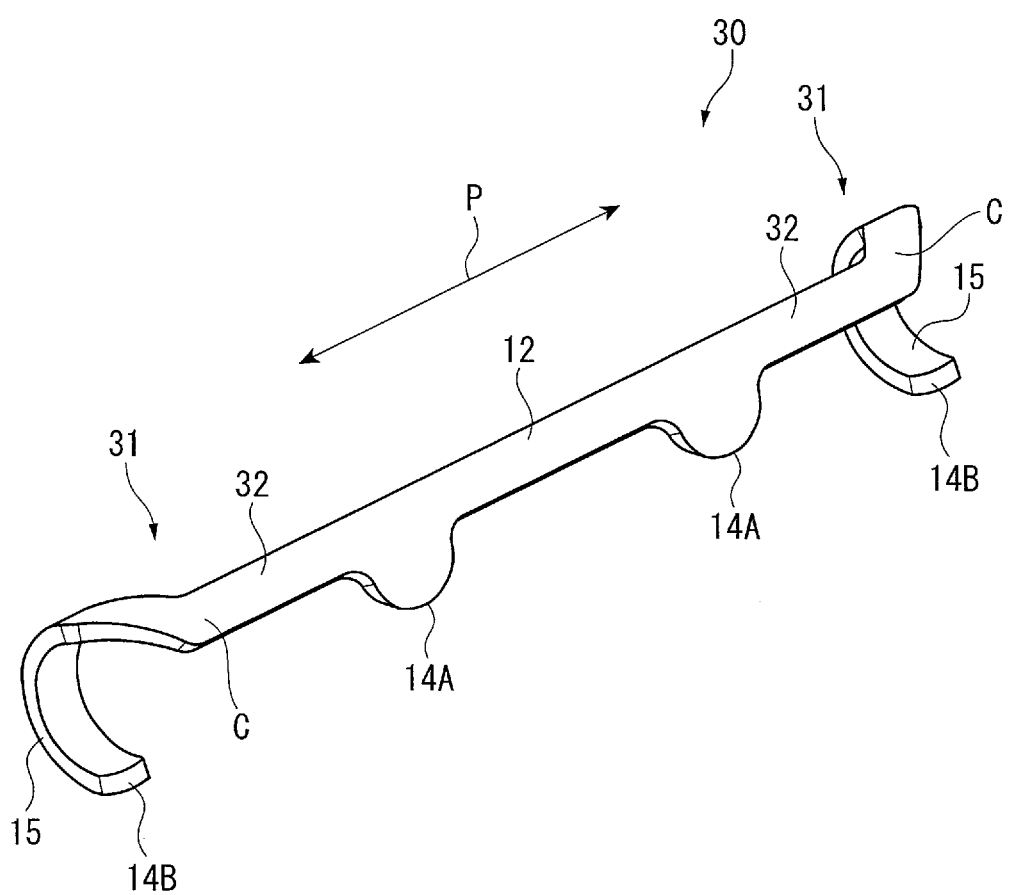
FIG. 12 is a perspective view showing the nail correcting device according to the third exemplary embodiment.
Figure 13:
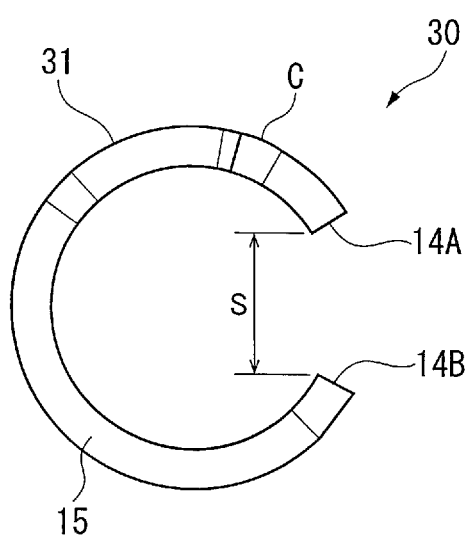
FIG. 13 is a side view showing the nail correcting device according to the third exemplary embodiment.
Figure 14:
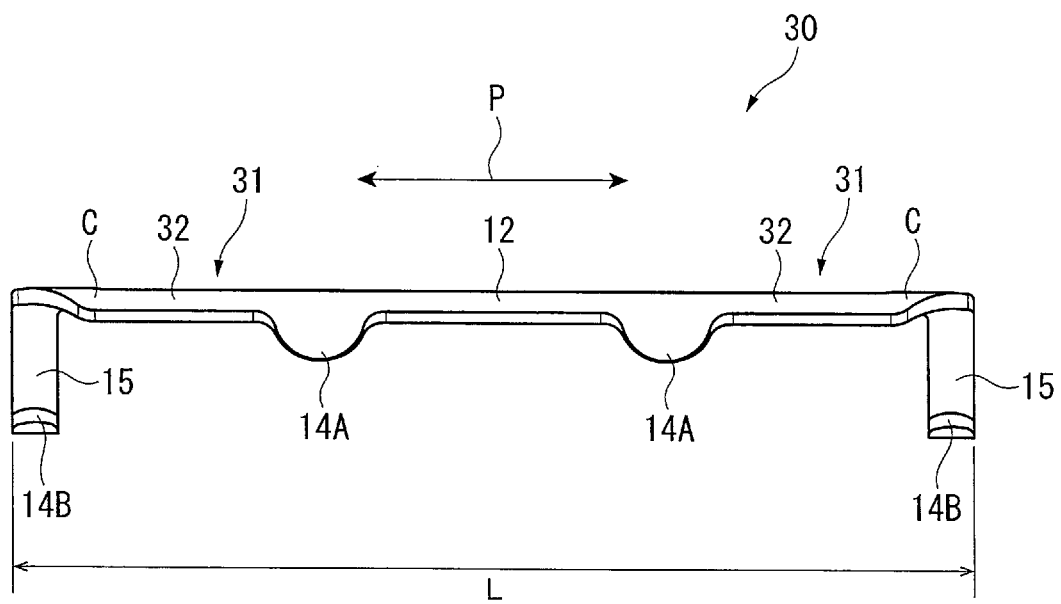
FIG. 14 is a front view showing the nail correcting device according to the third exemplary embodiment.
Figure 15:
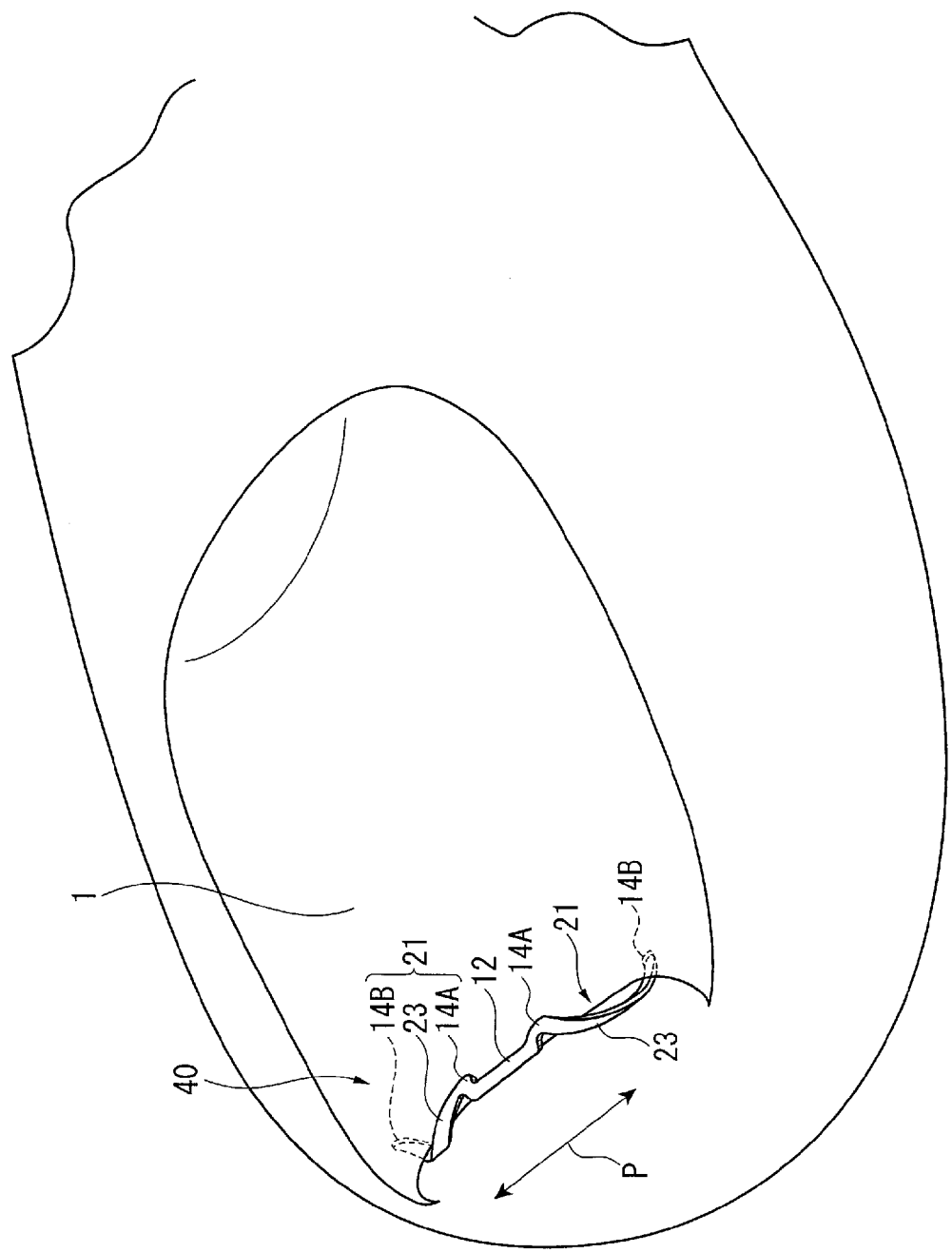
FIG. 15 is a perspective view showing a nail correcting device according to a fourth exemplary embodiment of the invention attached to a nail.
Figure 16:
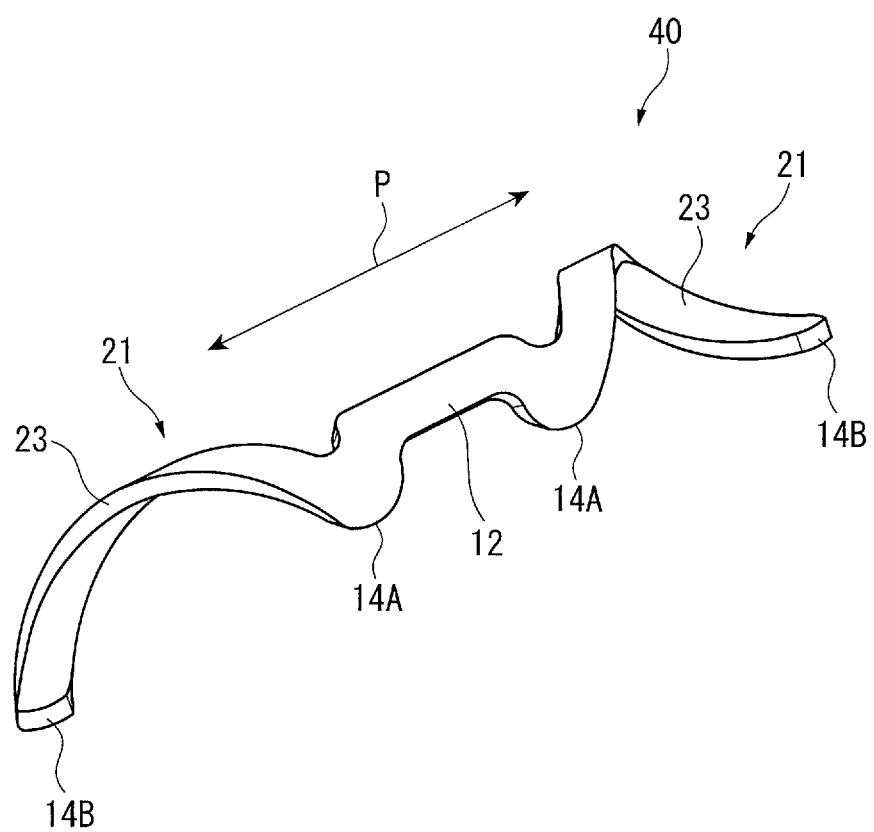
FIG. 16 is a perspective view showing the nail correcting device according to the fourth exemplary embodiment.
Figure 17:
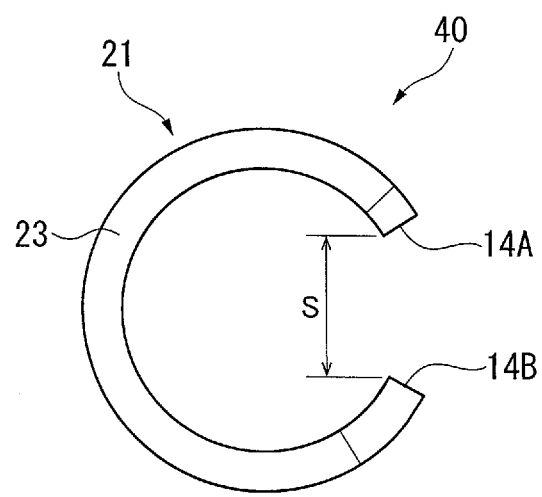
FIG. 17 is a side view showing the nail correcting device according to the fourth exemplary embodiment.
Figure 18:
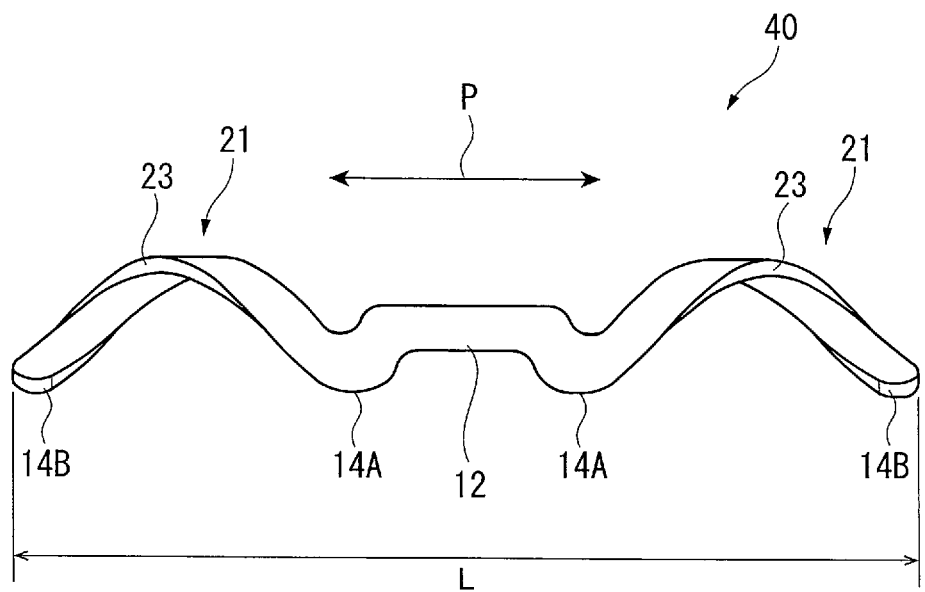
FIG. 18 is a front view showing the nail correcting device according to the fourth exemplary embodiment.

FIG. 10 schematically shows an analysis result of the nail correcting device 20 of the second exemplary embodiment by a finite element method. It should be noted that the nail correcting device shown in FIG. 10 is different from the nail correcting device of the second exemplary embodiment in the helical shape of the body, which has no influence on the analysis result.

In FIG. 10, reference signs F0, F1, F2 . . . F8 and F9 denote positions in the nail. Of the above positions in the nail, ones where stress acts on the nail correcting device 20 are denoted by reference signs E1, E2 and E3 in the descending order of the intensity of the stress. Reference signs QA, QB (arrows from the positions F2, F8) show nail corrective forces generated at the maximum curvature. The corrective forces QA, QB were each approximately 3 N.

As is evident from FIG. 10, it has been demonstrated that the corrective force QA (the maximum value) is generated at a position corresponding to the distal edge 14A, and the corrective force QB (the maximum value) is generated at a position corresponding to the distal edge 14B in the second exemplary embodiment. The corrective forces QA, QB acts in mutually opposite directions. It should be noted that merely the corrective forces acting on the half of the nail are described above with reference to FIG. 10, but the same applies to the other half.

The nail correcting device 20 of the second exemplary embodiment (shown in FIGS. 6 to 10) is manufactured and attached to the nail 1 in the same manners as that of the first exemplary embodiment.

The second exemplary embodiment can provide the following effect (6) in addition to the effects (1), (2), (4) and (5) of the first exemplary embodiment.

(6) The connecting piece 22 is the V-shaped portion, and has the distal ends each connected to the distal edge 14A situated at the inner side, the V-shaped portion being helical and having the same diameter as that of the body 13. Further, the base end 22B of the connecting piece 22 holds the nail 1 in combination with the distal edge 14A. The nail 1 can thus be firmly held not only by the pair of distal edges 14A, 14B, but also by the base end 22B.

Third Exemplary Embodiment

Next, a third exemplary embodiment of the invention will be described with reference to FIGS. 11 to 14.

As shown in FIGS. 11 to 14, a nail correcting device 30 of the third exemplary embodiment includes a pair of holding pieces 31 arranged side by side in the direction P, and the connecting piece 12 connecting the holding pieces 31. The whole of the nail correcting device 30 is made of a superelastic material.

The holding pieces 31 each include an arc portion 15, and a linear portion 32 having a first end connected to an end of the arc portion 15 and a second end connected to the distal edge 14A situated at the inner side.

The linear portion 32 is in alignment with the connecting piece 12. The arc portion 15 at the first end of the linear portion 32 is in an arc within the plane orthogonal to the direction P. A corner C where the arc portion 15 and the linear portion 32 are connected to each other is close to the distal edge 14B.

The linear portion 32 and the connecting piece 12 have the same width. A connecting portion between the linear portion 32 and the connecting piece 12 has a first side and a second side opposite to the first side, the first side being projected to define the distal edge 14A, the second side being linear in the longitudinal direction.

The nail correcting device 30 of the third exemplary embodiment is manufactured and attached to the nail 1 in the same manners as that of the first exemplary embodiment.

The third exemplary embodiment can provide the following effects (7) and (8) in addition to the effects (1) to (4) of the first exemplary embodiment.

(7) The holding piece 31 includes the linear portion 32 connected to the distal edge 14A situated at the inner side and linear along the longitudinal direction of the connecting piece 12. Since the connecting piece 12 and the linear portion 32 are in alignment with each other, the structure of the nail correcting device 30 can be further simplified.

(8) The arc portion 15 is defined within a plane orthogonal to the longitudinal direction of the linear portion 32, so that the corner C where the linear portion 32 and the arc portion 15 are connected to each other is close to the distal edge 14B connected to the end of the arc portion 15. Since the corner C can serve as a mark for attaching the nail correcting device 30 to the nail 1, the nail correcting device 30 can be easily attached to the nail 1.

Fourth Exemplary Embodiment

Next, a fourth exemplary embodiment of the invention will be described with reference to FIGS. 15 to 19.

As shown in FIGS. 15 to 18, a nail correcting device 40 of the fourth exemplary embodiment includes the pair of holding pieces 21 of the second exemplary embodiment, and the connecting piece 12 of the first exemplary embodiment. The whole of the nail correcting device 40 is made of a superelastic material.

The holding pieces 21 each include a body 23 including a helical portion. The body 23 has a first end connected to the distal edge 14A and a second end connected to the distal edge 14B. The distal edges 14A of the holding pieces 21 situated at the inner side are connected to both ends of the linear connecting piece 12.

Figure 19:
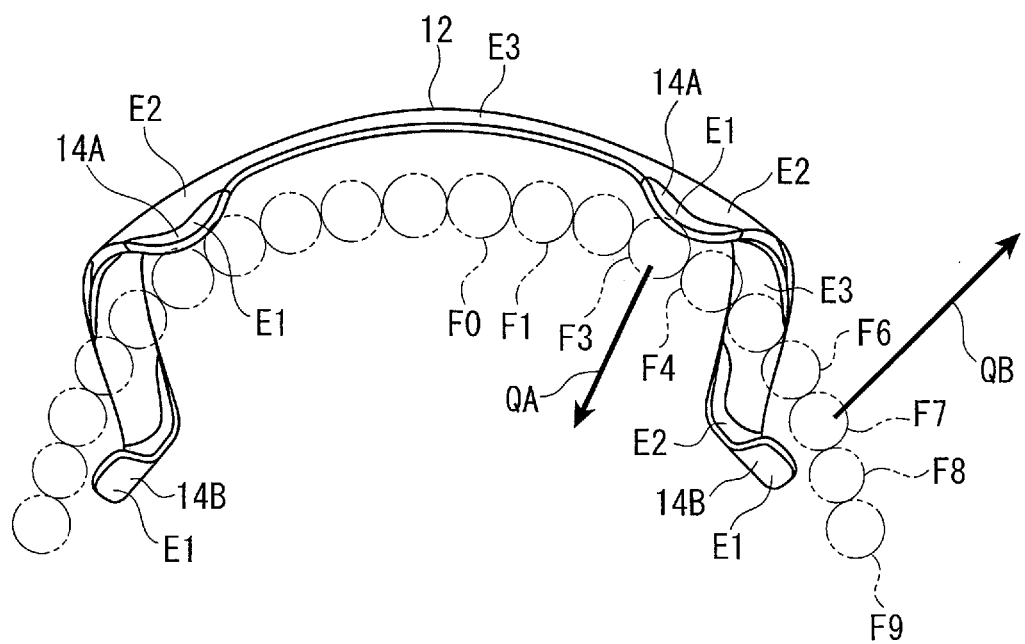
FIG. 19 schematically shows an analysis result by a finite element method according to the fourth exemplary embodiment.

FIG. 19 schematically shows an analysis result of the nail correcting device 40 of the fourth exemplary embodiment by a finite element method.

In FIG. 19, reference signs F0, F1, F2 . . . F8 and F9 denote positions in the nail. Of the above positions in the nail, ones where stress acts on the nail correcting device 40 are denoted by reference signs E1, E2 and E3 in the descending order of the intensity of the stress. Reference signs QA, QB (arrows from the positions F3, F7) show nail corrective forces generated at the maximum curvature. The corrective forces QA, QB were each approximately 3 N.

As is evident from FIG. 19, it has been demonstrated that the corrective force QA (the maximum value) is generated at a position corresponding to the distal edge 14A, and the corrective force QB (the maximum value) is generated at a position corresponding to the distal edge 14B in the fourth exemplary embodiment. It should be noted that merely the corrective forces acting on the half of the nail are described above with reference to FIG. 19, but the same applies to the other half.

The nail correcting device 40 of the fourth exemplary embodiment is manufactured and attached to the nail 1 in the same manners as that of the first exemplary embodiment.

The fourth exemplary embodiment can provide the effects (1) to (3) and (5) of the first exemplary embodiment.

Incidentally, it should be understood that the scope of the invention is not limited to the above-described exemplary embodiments but includes modifications and improvements compatible with the invention.

For instance, in the exemplary embodiments, the nail correcting devices 10, 20, 30, 40 are each made of a superelastic material, but may each be an elastic body with shape-memory properties instead of being an elastic body of a superelastic material. Further, elastic bodies made of elastic materials such stainless steel, titanium alloy, copper alloy and iron, and elastic materials such as plastics are also available.

What is claimed is:

1. A nail correcting device made of an elastic material, the nail correcting device comprising:
    a pair of linear holding pieces arranged side by side in a predetermined direction; and
    a connecting piece connecting the holding pieces to each other, the pair of holding pieces each comprising:
    a body at least partly in an arc within a plane perpendicular to the predetermined direction; and
    a pair of first and second distal edges connected to both ends of the body to hold a nail, the pair of first and second distal edges being spaced from each other along the predetermined direction at an inner side and an outer side, wherein
    each body comprises a helical portion having an end connected to the first distal edge at the inner side of each of the pair of holding pieces, and
    an axial center of the helical portions share a common longitudinal axis.

2. The nail correcting device according to claim 1, wherein the connecting piece extends in the predetermined direction, and has ends each connected to the first distal edge at the inner side of each of the pair of holding pieces.

3. The nail correcting device according to claim 2, wherein the body comprises an arc portion in an arc within a plane orthogonal to the predetermined direction, the arc portion being connected to the second distal edge at the outer side of each of the pair of holding pieces.

4. The nail correcting device according to claim 1, wherein the body comprises a linear portion provided along a longitudinal direction of the connecting piece, the linear portion having an end connected to the first distal edge at the inner side of each of the pair of holding pieces.

5. The nail correcting device according to claim 1, wherein the connecting piece comprises a V-shaped portion having distal ends and a base end, the distal ends being each connected to the first distal edge at the inner side of each of the pair of the holding pieces, the base end holding the nail in combination with the first distal edge of each of the pair of the holding pieces.

* * * * *